US012622861B2

(12) United States Patent
Hiban et al.

(10) Patent No.: US 12,622,861 B2
(45) Date of Patent: May 12, 2026

(54) STABLE WASH COMPOSITION

(71) Applicant: Conopco, Inc., Englewood Cliffs, NJ (US)

(72) Inventors: Douglas John Hiban, Newtown, CT (US); Tirucherai Varahan Vasudevan, Bethany, CT (US)

(73) Assignee: Conopco, Inc., Hoboken, NJ (US)

( * ) Notice: Subject to any disclaimer, the term of this patent is extended or adjusted under 35 U.S.C. 154(b) by 251 days.

(21) Appl. No.: 18/036,445

(22) PCT Filed: Nov. 8, 2021

(86) PCT No.: PCT/EP2021/080983
§ 371 (c)(1),
(2) Date: May 11, 2023

(87) PCT Pub. No.: WO2022/101147
PCT Pub. Date: May 19, 2022

(65) Prior Publication Data
US 2023/0398050 A1     Dec. 14, 2023

(30) Foreign Application Priority Data

Nov. 13, 2020     (EP) ..................................... 20207636

(51) Int. Cl.
*A61K 8/00*     (2006.01)
*A61K 8/73*     (2006.01)
*A61Q 19/10*     (2006.01)

(52) U.S. Cl.
CPC ................ *A61K 8/73* (2013.01); *A61Q 19/10* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 5,009,814 A | 4/1991 | Kelkenberg et al. | |
| 5,389,279 A | 2/1995 | Au et al. | |
| 5,393,466 A | 2/1995 | Ilardi et al. | |
| 6,444,629 B1 | 9/2002 | Elliott et al. | |
| 2004/0097385 A1 | 5/2004 | Chen et al. | |
| 2009/0137438 A1* | 5/2009 | Lepilleur ................. | C08L 1/26 |
| | | | 510/121 |
| 2012/0183484 A1* | 7/2012 | Beaumer ............... | A61K 8/042 |
| | | | 424/70.13 |
| 2016/0000669 A1 | 1/2016 | Hinman et al. | |
| 2018/0177708 A1 | 6/2018 | Lee et al. | |
| 2019/0008738 A1 | 1/2019 | Hardy et al. | |
| 2019/0359735 A1 | 11/2019 | Fischer et al. | |

FOREIGN PATENT DOCUMENTS

| | | |
|---|---|---|
| FR | 2683720 | 5/1993 |
| FR | 2954162 | 6/2011 |
| WO | WO2011032728 | 3/2011 |

OTHER PUBLICATIONS

Search Report and Written Opinion in EP20207636; May 18, 2021.
Search Report and Written Opinon in PCTEP2021080983; Feb. 25, 2022.

* cited by examiner

*Primary Examiner* — Necholus Ogden, Jr.
(74) *Attorney, Agent, or Firm* — Edward A. Squillante, Jr.

(57)     ABSTRACT

The invention is directed to a stable composition wash composition. The wash composition comprises a mixture of naturally derived and biodegradable sulfated polysaccharides. The wash composition has a viscosity of 40,000 cps or less, and surprisingly, is free of syneresis, discoloration and malodor, even after being stored at elevated temperatures.

19 Claims, No Drawings

STABLE WASH COMPOSITION

FIELD OF THE INVENTION

The present invention is directed to a stable wash composition. More particularly, the invention is directed to a wash composition comprising water, surfactant and a mixture of naturally derived and biodegradable sulfated polysaccharides. The wash composition has a viscosity of 40,000 cps or less, and surprisingly, is free of syneresis, discoloration and malodor, even after being stored at elevated temperatures.

BACKGROUND OF THE INVENTION

Personal care compositions are typically employed to cleanse skin and to reduce shine associated with sebum produced in specialized epithelial cells known as sebocytes. They are also used to minimize bacteria on the hands and face such that washing is viewed as the most effective way to prevent the spread of germs and bacteria. In fact, experts believe that periodic washing throughout the day can reduce the number of consumers catching colds by about 50%.

Consumers know it is generally good practice to regularly clean their hands and not touch their face in order to minimize the risk of getting sick. During epidemics, such as the one caused by ebola, and pandemics like those caused by influenza, cholera and HIV/AIDS, consumers are well aware that these serious infectious diseases are best defeated with regimens that include medical treatment, social distancing, the use of face masks and extensive hand washing. Information provided by the Centers for Disease Control and Prevention suggests that the COVID-19 (coronavirus) pandemic is a direct result of a virus that is more efficient and severe than influenza and that spreads rapidly from person to person via respiratory droplets. During such a pandemic, consumers know it is in their best interest to consistently wash their hands and face.

With the need to wash more often, it is highly desirable to develop wash compositions that are not only good for the consumer but also safe for the environment. This invention, therefore, is directed to a stable wash composition comprising water, surfactant and a mixture of naturally derived and biodegradable sulfated polysaccharides. The wash composition has a viscosity of 40,000 cps or less, and is surprisingly free of syneresis, discoloration and malodor even after being stored at elevated temperatures.

Additional Information

Efforts have been disclosed for making wash compositions. In U.S. Patent Application No. 2019/008738A1, personal care compositions with cationic surfactant, nonionic surfactant and a polyacrylate cross-polymer structuring agent are described. The wash compositions can include carrageenan as a thickener.

Other efforts have been described for making wash compositions. In U.S. Patent Application No. 2019/0359735A1, water soluble hybrid polymers suitable for use in a body wash are described.

Still other efforts have been described for making wash compositions. In U.S. Pat. No. 6,444,629, personal cleansing compositions with good rinse feel and skin mildness are described.

None of the additional information describes a composition with a mixture of biodegradable sulfated polysaccharides as claimed herein.

SUMMARY OF THE INVENTION

In a first aspect, the present invention is directed to a wash composition concentrate comprising:
a) 0.5 to 3.0% by weight of a hydrocolloid mixture of sulfated polysaccharide;
b) 1.5 to 50% by weight surfactant;
c) 0.0 to 50% by weight polyol; and
d) water,
the wash composition concentrate being flowable and the mixture of sulfated polysaccharide comprising lambda to iota carrageenan in a weight ratio from 1:1 to 1:7, and preferably, from 1:1 to 1:6, and most preferably, from 1:1 to 1:5.5, the sulfated polysaccharide mixture being at least 50% by weight of a mixture of lambda and iota carrageenan based on total weight of the mixture of sulfated polysaccharide in the concentrate.

In a second aspect, the present invention is directed to a wash composition comprising:
a) 0.35 to 1.5% by weight of a hydrocolloid mixture of sulfated polysaccharide (at least 50% 70 80 90 lambda and iota of the total weight of the composition);
b) 0.75 to 25% by weight surfactant;
c) 0.0 to 25% by weight polyol; and
d) water,
the wash composition having a viscosity of 40,000 cps or less and the mixture of sulfated polysaccharide comprising lambda to iota carrageenan in a weight ratio from 1:1 to 1:7, and preferably, from 1:1 to 1:6, and most preferably, from 1.1 to 1:5.5, the sulfated polysaccharide mixture being at least 50% by weight of a mixture of lambda and iota carrageenan based on total weight of sulfated polysaccharide in the wash composition.

In a third aspect, the present invention is directed to a method for washing with the wash composition of the second aspect of the invention.

In a fourth aspect, the invention is directed to the use of a mixture of lambda and iota carrageenan to thicken and stabilize a wash composition.

All other aspects of the present invention will more readily become apparent from the description and examples which follow.

Skin, as used herein, is meant to include skin on the arms (including underarms), face, feet, neck, chest, hands, legs, buttocks and scalp (including hair). Hydrocolloid is meant to mean a polysaccharide that thickens or gels in the presence of water. Wash composition concentrate means a flowable composition comprising 30% by weight to 55% by weight water that can be diluted with water (with or without a water miscible solvent, like glycerine) to produce the wash composition of the invention. Flowable means pourable at 25° C. The wash composition of the present invention is preferably transparent or translucent, and therefore, preferably isotropic. The hydrocolloid mixture of sulfated polysaccharide is at least 50% by weight of a mixture of lambda and iota carrageenan based on total weight of sulfated polysaccharide in the wash concentrate and composition. In an embodiment of the invention, the hydrocolloid mixture of sulfated polysaccharide is at least 60%, and preferably, at least 70%, and most preferably, at least 80% by weight of a mixture of lambda and iota carrageenan based on total weight of sulfated polysaccharide in the concentrate and wash composition. In still another embodiment, the hydrocolloid mixture of sulfated polysaccharide is 80 to 95%, and preferably, 84 to 92% by weight of a mixture of lambda and iota carrageenan based on total weight of sulfated polysaccharide in the concentrate and wash composition.

In an optional embodiment of the invention, kappa carrageenan makes up no more than 20% by weight of the total weight of carrageenan in the wash concentrate and composition, and preferably, no more than 15.0%, and most preferably, from 0.0001 to no more than 10.0% by weight of carrageenan in the concentrate and wash composition. In an embodiment of the invention, the concentrate and wash composition have no (0.0% by weight) kappa carrageenan. The wash composition of the present invention is suitable to be a home care composition, shampoo, make-up wash, facial wash or personal care and liquid body wash. Preferably, the wash composition of the present invention is a body wash that is ready for topical application and to be wiped or washed off, and preferably, washed off with water. The wash composition may, optionally, comprise medicinal or therapeutic agents, but preferably, is a wash which is a cleaning and/or cosmetic wash that is a non-therapeutic wash to wash of, for example, dirt, oils, and/or bacteria that can cause malodour. As hereinafter described, the wash composition of the present invention may optionally comprise skin benefit ingredients added thereto such as vitamins and/or derivatives thereof, resorcinols, retinoic acid precursors, colorants, moisturizers, sunscreens, mixtures thereof or the like. The skin benefit ingredients (or agents) may be water or oil soluble. If used, oil soluble skin benefit agents typically make up to 1.0% by weight of the wash composition whereby water-soluble skin benefit agents, when used, typically make up to 10% by weight of the wash composition. The wash composition typically has a pH from 3.5 to 10.0, and preferably, 4 to 8, and most preferably, 5.0 to 7.5. In an embodiment of the invention, the pH of the wash composition can be 5.5 to 7.3, including all ranges subsumed therein. Viscosity, unless noted otherwise, is taken with a Discovery HR-2 Rheometer using sand blasted plates having a 1000 micron gap and a first shear rate $S_A$ of 4 s$^{-1}$ for a first viscosity $V_A$ and a second shear rate $S_B$ of 10 s$^{-1}$ for a second viscosity $V_B$, both at 25° C. and 20 second intervals. Viscosity is reported in Pascal seconds (1 Pascal second=1000 centipoise (cps)). Stable, as used herein, means no phase separation, discoloration and malodour generation from the wash composition after being stored for at least two (2) weeks at 50° C., and preferably, at least one (1) month at 45° C., and more preferably, from 2 to 4 months at 45° C. The term comprising is meant to encompass the terms consisting essentially of and consisting of. For the avoidance of doubt, and for illustration, the composition of this invention comprising surfactant, water and hydrocolloid is meant to include a composition consisting essentially of the same and a composition consisting of the same. Except in the operating comparative examples, or where otherwise explicitly indicated, all numbers in this description indicating amounts or ratios of materials or conditions and/or physical properties of materials and/or use are to be understood as modified by the word "about". All ranges defined herein are meant to include all ranges subsumed therein unless otherwise stated.

DETAILED DESCRIPTION OF THE INVENTION

As to the hydrocolloid mixture of sulfated polysaccharide suitable for use in the present invention, the same comprises lambda and iota carrageenan. In an embodiment of the invention, the hydrocolloid mixture of sulfated polysaccharide consists essentially of lambda and iota carrageenan. In yet another embodiment of the invention, the hydrocolloid mixture of sulfated polysaccharide consists of lambda and iota carrageenan.

Typically, the wash composition of the present invention will comprise from 0.25 to 1.5% by weight of the hydrocolloid mixture, and preferably, from 0.3 to 1.4%, and most preferably, from 0.4 to 1.3% by weight of the mixture. Such mixture typically comprises lambda to iota carrageenan in a weight ratio from 1:1 to 1:7, and preferably, from 1:1 to 1:6, and most preferably, from 1:1 to 1:5.5. In an embodiment of the invention the hydrocolloid mixture consists essentially of lambda and iota carrageenan in a weight ratio from 1:2 to 1:4 and still in another embodiment from 1:2.7 to 1:3.4. In yet another embodiment the mixture consists of lambda and iota carrageenan in a weight ratio from 1:2 to 1:4 and still in another embodiment from 1:2.7 to 1:3.4.

Regarding the surfactants that may be used, the same are limited only to the extent that they are suitable for use in compositions that are topically applied to a surface, preferably skin.

Anionic surfactants suitable for use in the wash composition of the present invention include aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of at least 1.0, preferably less than 5, and most preferably 1 to 4, and M is a solubilizing cation such as sodium, potassium, ammonium or substituted ammonium.

The anionic may also include alkyl sulfosuccinates (including mono- and dialkyl, e.g., $C_8$-$C_{22}$ sulfosuccinates); acyl taurates (often methyl taurates), acyl sarcosinates, sulfoacetates, $C_8$-$C_{22}$ alkyl phosphates and phosphonates, alkyl phosphate esters and alkoxyl alkyl phosphate esters, acyl lactates, $C_8$-$C_{22}$ monoalkyl succinates and maleates, alkyl glucosides and acyl isethionates, and the like.

Sulfosuccinates may be monoalkyl sulfosuccinates having the formula:

$$R^1O_2CCH_2CH(SO_3M)CO_2M;$$

and amide-MEA sulfosuccinates of the formula:

$$R^1CONHCH_2CH_2O_2CCH_2CH(SO_3M)CO_2M \text{ wherein } R^1 \text{ ranges from } C_8\text{-}C_{22} \text{ alkyl.}$$

Sarcosinates are generally indicated by the formula:

$$R^2CON(CH_3)CH_2CO_2M, \text{ wherein } R^2 \text{ ranges from } C_8\text{-}C_{20} \text{ alkyl.}$$

Taurates are generally identified by formula:

$$R^3CONR^4CH_2CH_2SO_3M$$

wherein $R^3$ is a $C_8$-$C_{20}$ alkyl, $R^4$ is a $C_1$-$C_4$ alkyl.

M is a solubilizing cation as previously described. The isethionates that may be used include $C_8$-$C_{18}$ acyl isethionates (including those which have a substituted head group such as a $C_{1-4}$ alkyl substitution, preferably methyl substitution). These esters are prepared by a reaction between alkali metal isethionate with mixed aliphatic fatty acids having from 6 to 18 carbon atoms and an iodine value of less than 20. Often at least 75% of the mixed fatty acids have from 12 to 18 carbon atoms and up to 25% have from 6 to 10 carbon atoms.

The acyl isethionate suitable for use may be an alkoxylated isethionate such as is described in Ilardi et al., U.S. Pat. No. 5,393,466, entitled "Fatty Acid Esters of Polyalkoxylated isethonic acid; issued Feb. 28, 1995; hereby incorporated by reference. This compound has the general formula:

$$R^5C—O(O)—C(X)H—C(Y)H—(OCH_2—CH_2)_m—$$
$$SO_3M$$

wherein $R^5$ is an alkyl group having 8 to 18 carbons, m is an integer from 1 to 4, X and Y are each independently hydrogen or an alkyl group having 1 to 4 carbons and M is a solubilizing cation as previously described.

In an embodiment of the invention, an anionic surfactant suitable for use is sodium lauroyl glycinate, sodium cocoyl glycinate, sodium lauroyl glutamate, sodium cocoyl glutamate, sodium lauroyl isethionate, sodium cocoyl isethionate, sodium methyl lauroyl taurate, sodium methyl cocoyl taurate or a mixture thereof. Such anionic surfactants are commercially available from suppliers like Galaxy Surfactants, Clariant, Sino Lion and Innospec. Sodium cocoyl isethionate, sodium methyl lauroyl taurate, sodium lauroyl glycinate, sodium methyl lauroyl isethionate or mixtures thereof are the preferred anionics suitable for use. In an embodiment of the invention, the anionic surfactant used is typically at least one of sodium lauroyl glutamate, sodium cocoyl isethionate, and/or sodium methyl lauroyl taurate. In a preferred embodiment, the anionic surfactant used in the wash composition of this invention is sodium lauroyl glutamate.

Amphoteric surfactants suitable for use in the invention (which depending on pH can be zwitterionic) include sodium acyl amphoacetates, sodium acyl amphopropionates, disodium acyl amphodiacetates and disodium acyl amphodipropionates where the acyl (i.e., alkanoyl group) can comprise a $C_7$-$C_{18}$ alkyl portion. Illustrative examples of the amphoteric surfactants suitable for use include sodium lauroamphoacetate, sodium cocoamphoacetate, sodium lauroamphoacetate, sodium cocoamphoacetate or mixtures thereof.

As to the zwitterionic surfactants that may be employed in the wash compositions of the present invention, such surfactants include at least one acid group. Such an acid group may be a carboxylic or a sulphonic acid group. They often include quaternary nitrogen, and therefore, can be quaternary amino acids. They should generally include an alkyl or alkenyl group of 7 to 18 carbon atoms generally comply with an overall structural formula:

$$R^6—[—C(O)—NH(CH_2)_q—]_r—N^+—(R^7—)(R^8)A-B$$

where $R^6$ is alkyl or alkenyl of 7 to 18 carbon atoms; $R^7$ and $R^8$ are each independently alkyl, hydroxyalkyl or carboxyalkyl of 1 to 3 carbon atoms; q is 2 to 4; r is 0 to 1; A is alkylene of 1 to 3 carbon atoms optionally substituted with hydroxyl, and B is —$CO_2$— or —$SO_3$—.

Suitable zwitterionic surfactants that may be used in the present invention and within the above general formula include simple betaines of formula:

$$R^6—N^+—(R^7)(R^8)CH_2CO_2^-$$

and amido betaines of formula:

6

$$R^6—CONH(CH_2)_t—N^+—(R^7)(R^8)CH_2CO_2^-$$

where t is 2 or 3.

In both formulae $R^6$, $R^7$ and $R^8$ are as defined previously. $R^6$ may, in particular, be a mixture of $C_{12}$ and $C_{14}$ alkyl groups derived from coconut oil so that at least half, preferably at least three quarters of the groups $R^6$ have 10 to 14 carbon atoms. $R^7$ and $R^8$ are preferably methyl.

A further possibility is that the zwitterionic surfactant is a sulphobetaine of formula:

$$R^6—N^+—(R^7)(R^8)(CH_2)_3SO_3^-$$

or $$R^6—CONH(CH_2)_u—N^+—(R^7)(R^8)(CH_2)_3SO_3^-$$

where u is 2 or 3, or variants of these in which —$(CH_2)_3SO_3^-$ is replaced by $$CH_2C(OH)(H)CH_2SO_3^-.$$

In these formulae, $R^6$, $R^7$ and $R^8$ are as previously defined.

Illustrative examples of the zwitterionic surfactants suitable for use include betaines like cocodimethyl carboxymethyl betaine, cocamidopropyl betaine and laurylamidopropyl betaine. An additional zwitterionic surfactant suitable for use includes cocamidopropyl hydroxy sultaine. Such surfactants are made commercially available from suppliers like Stepan Company, and it is within the scope of the invention to employ mixtures of the aforementioned surfactants. In a preferred embodiment, the zwitterionic surfactant used in the wash composition of this invention is cocamidopropyl betaine.

Nonionic surfactants may be used in the wash composition of the present invention. When used, nonionic surfactants are typically used at levels as low as 0.5, 1, 1.5 or 2% by weight and at levels as high as 6, 8, 10 or 12% by weight of the wash composition. The nonionics which may be used include, in particular, the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic surfactant compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other nonionic surfactants include long chain tertiary amine oxides, long chain tertiary phosphine oxides, dialkyl sulphoxides, and the like.

In an embodiment of the invention, nonionic surfactants optionally used can include fatty acid/alcohol ethoxylates having the following structures a) $HOCH_2(CH_2)_s$ $(CH_2CH_2O)_vH$ or b) $HOOC(CH_2)_c(CH_2CH_2O)_dH$; where s and v are each independently an integer up to 18; and c and d are each independently an integer from 1 or greater. In an embodiment of the invention, s and v are each independently 6 to 18; c and d are each independently 1 to 30. Other options for nonionic surfactants include those having the formula $HOOC(CH_2)_i—CH=CH—(CH_2)_k(CH_2CH_2O)_zH$, where i, k are each independently 5 to 15; and z is 5 to 50. In another embodiment of the invention, i and k are each independently 6 to 12; and z is 15 to 35.

The nonionic may also include a sugar amide, such as a polysaccharide amide. Specifically, the surfactant may be one of the lactobionamides described in U.S. Pat. No. 5,389,279 to Au et al., entitled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

In an embodiment of the invention, cationic surfactants may optionally be used in the wash composition of the present invention.

One class of optional cationic surfactants includes heterocyclic ammonium salts such as cetyl or stearyl pyridinium chloride, alkyl amidoethyl pyrrylinodium methyl sulfate, and lapyrium chloride.

Tetra alkyl ammonium salts are another useful class of cationic surfactants suitable for optional use. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides, and behenyl dimethyl ammonium chloride.

Still other types of cationic surfactants that may be used are the various ethoxylated quaternary amines and ester quats. Examples include PEG-5 stearyl ammonium lactate (e.g., Genamin KSL manufactured by Clariant), PEG-2 coco ammonium chloride, PEG-15 hydrogenated tallow ammonium chloride, PEG 15 stearyl ammonium chloride, dipalmitoyl ethyl methyl ammonium chloride, dipalmitoyl hydroxyethyl methyl sulfate, and strearyl amidopropyl dimethylamine lactate.

Even other useful cationic surfactants suitable for optional use include quaternized hydrolysates of silk, wheat, and keratin proteins, and it is within the scope of the invention to use mixtures of the aforementioned cationic surfactants.

If used, cationic surfactants will make up no more than 1.0% by weight of the wash composition. When present, they typically make up from 0.01 to 0.7%, and more typically, from 0.1 to 0.5% by weight of the wash composition, including all ranges subsumed therein.

In an embodiment of this invention, the wash composition will be substantially free of polymeric quaternary ammonium compounds (including salts of the same). In another embodiment, the wash composition will comprise less than 0.1% by weight polymeric quaternary ammonium compounds. In yet another embodiment, the wash composition comprises less than 0.01% by weight polymeric quaternary ammonium compounds. In even another embodiment, the wash composition is free of polymeric quaternary ammonium compounds (i.e., 0.0%).

Surfactant typically makes up from 0.75 to 25%, and preferably, from 2 to 20%, and most preferably, from 6 to 15% by weight of the wash composition. In an embodiment of the invention, surfactant makes up from 7 to 12% by weight of the wash composition. As to the composition concentrate, the same comprises from 1.5 to 50%, and preferably, from 2 to 40%, and most preferably, from 12 to 30% by weight surfactant. In an embodiment of the invention, the composition concentrate comprises from 14 to 24% by weight surfactant.

In still another embodiment of the invention, the wash composition of the present invention has surfactant that is anionic, amphoteric, zwitterionic or a mixture thereof. In yet another embodiment, the surfactant is an isethionate, taurate, betaine or a mixture thereof. In even another embodiment, the surfactant used in the wash composition is a mixture of cocamidopropyl betaine, sodium lauroyl isethionate and sodium methyl lauroyl taurate.

Water typically makes up from 60 to 95%, and preferably, from 70 to 90%, and most preferably, from 70 to 85% by weight of the wash composition, including all ranges subsumed therein. As to the concentrate, the same typically has from 30 to 55%, and preferably, from 35 to 50%, and most preferably, from 35 to 45% by weight water wherein the same may be diluted with water or water and a water miscible solvent, to produce the wash composition of the present invention. In an embodiment of the invention, if water miscible solvent, like a polyol, is used to dilute the concentrate with water, the polyol makes up from 1 to 15%, and preferably, from 2 to 10%, and most preferably, from 3 to 8% by weight of the total weight of water and miscible solvent used to dilute the concentrate.

Adjusters suitable to modify/buffer the pH may be used. Such pH adjusters include triethylamine, NaOH, KOH, $H_2SO_4$, HCl, $C_6H_8O_7$ (i.e., citric acid) or mixtures thereof. The pH adjusters are added at amounts to yield the desired final pH. The pH values may be assessed with commercial instrumentation such as a pH meter made commercially available from Thermo Scientific®.

Polyols suitable for use in the wash composition present invention are limited only to the extent that they are usable in a wash composition for topical application. Illustrative and non-limiting examples of the polyols suitable for use in the present invention include sorbitol, glycerol, mannitol, xylitol, maltitol or mixtures thereof. In an embodiment of the invention, the polyol used is at least 50% by weight glycerol, based on total weight of the polyol used in the wash composition. In another embodiment of the invention, the polyol used is all glycerol (100% by weight). Polyol will typically make up from 0.0 to 25% by weight of the wash composition, and preferably, from 0.5 to 8% by weight of the wash composition, and most preferably, from 0.75 to 3.5% by weight of the wash composition, including all ranges subsumed therein.

While not required, in addition to the hydrocolloid mixture of sulfated polysaccharide used in the present invention, it is within the scope of this invention to optionally use additional gelling or thickening agents like acrylates. If used, the acrylates include those generally classified as acrylic acid crosslinked with allyl sucrose or allyl pentaerythritol acrylic acid and $C_{10}$-$C_{30}$ alkyl acrylate crosslinked with allyl pentaerythritol. Such acrylates are sold under the Carbopol® name and are made commercially available by Lubrizol. Other acrylates suitable for use include those which are a copolymer formed from an ester of acrylic acid and ethoxylated palm alcohol with about 25 moles of ethylene oxide and one or more monomers of acrylic acid, methacrylic acid or one of their simple esters. These acrylates are sold, for example, under the Synthalen name, and made commercially available from suppliers like 3V. When used such optional thickeners will make up from 0.1 to 10%, and preferably, from 0.2 to 6% and most preferably, from 0.3 to 4% by weight of the total weight of hydrocolloid mixture of sulfated polysaccharide and optional gelling or thickening agents.

The viscosity of the wash composition (measured at 4 $s^{-1}$ for 20 seconds) of the present invention is 40,000 cps or less, and preferably, from 700 to 15,000 cps, and most preferably, from 1000 to 12,000 cps, including all ranges subsumed therein. As to the concentrate, the same has a viscosity that is from 10 to 60% greater, and preferably, from 15 to 50% greater, and most preferably, from 20 to 40% greater than the viscosity of the wash composition made from diluting or hydrating such concentrate.

Optional skin benefit agents suitable for use in the wash composition of this invention are limited only to the extent that they are capable of being topically applied, and suitable to dissolve in the wash composition at the desired pH.

Illustrative examples of the benefit agents suitable to include in the water portion of the wash composition are acids, like amino acids, such as arginine, valine or histidine. Additional water soluble benefit agents suitable for use include vitamin $B_2$, niacinamide (vitamin $B_3$), vitamin Br, vitamin C, mixtures thereof or the like. Water soluble derivatives of such vitamins may also be employed. For instance, vitamin C derivatives such as ascorbyl tetraisopalmitate, magnesium ascorbyl phosphate and ascorbyl glycoside may be used alone or in combination with each other. Other water-soluble benefit agents suitable for use include 4-ethyl resorcinol, extracts like sage, aloe vera, green tea, grapeseed, thyme, chamomile, yarrow, cucumber, liquorice, rosemary extract or mixtures thereof. Water soluble sunscreens like ensulizole may also be used. Total amount of optional water-soluble benefit agents (including mixtures) when present in the wash composition may range from 0.0 to 10%, preferably from 0.001 to 8%, and most preferably, from 0.01 to 6% by weight, based on total weight of the wash composition.

It is also within the scope of the present invention to optionally include oil soluble benefit agents. Such oil soluble actives or benefit agents can be solubilized in the surfactants used. The only limitation with respect to such oil soluble benefit agents are that the same are suitable to provide a benefit when topically applied.

Illustrative examples of the types of oil soluble benefit agents that may optionally be used in the compositions of this invention include components like stearic acid, vitamins like Vitamin A, D, E and K (and their oil soluble derivatives), sunscreens like ethylhexylmethoxycinnamate, bisethyl hexyloxyphenol methoxyphenol triazine, 2-ethyl-hexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Other optional oil soluble benefit agents suitable for use include resorcinols like 4-hexyl resorcinol, 4-phenylethyl resorcinol, 4-cyclopentyl resorcinol, 4-cyclohexyl resorcinol 4-isopropyl resorcinol or a mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol mixtures thereof or the like.

In an embodiment of the invention, the optional oil soluble benefit agent used is a retinoic acid precursor. In one embodiment of the invention, the retinoic acid precursor is retinol, retinal, retinyl propionate, retinyl palmitate, retinyl acetate or a mixture thereof. Retinyl propionate, retinyl palmitate and mixtures thereof are typically preferred.

When optional oil soluble active or benefit agent is used in the composition of the invention, such active typically makes up from 0.0 to 0.75%, and preferably, from 0.001 to 0.65%, and most preferably, from 0.05 to 0.35% by weight of the wash composition. In yet another embodiment, oil soluble benefit agent makes up from 0.1 to 0.5% by weight of the total weight of the wash composition.

Conventional preservatives can desirably be incorporated into the wash composition to protect against the growth of potentially harmful microorganisms. Cosmetic chemists are familiar with appropriate preservatives and routinely choose them to satisfy the preservative challenge test and to provide product stability. Suitable traditional preservatives for use include hydantoin derivatives and propionate salts. Particularly preferred preservatives are iodopropynyl butyl carbamate, phenoxyethanol, hydroxyacetophenone, ethylhexylglycerine, hexylene glycol, methyl paraben, propyl paraben, imidazolidinyl urea, sodium dehydroacetate, dimethyl-dimethyl (DMDM) hydantoin, sodium benzoate, benzyl alcohol and mixtures thereof. Other preservatives suitable for use include sodium dehydroacetate, chlorophenesin, decylene glycol, N-capryloyl glycine, N-undecylenoyl glycine and mixtures of the same. The preservatives should be selected having regard for the use of the composition and possible incompatibilities between the preservatives and other ingredients in the emulsion. Preservatives are preferably employed in amounts ranging from 0.01% to 2.0% by weight of the total weight of the wash composition, including all ranges subsumed therein. Also preferred is a preservative system that includes from 0.1 to 1.0% 1,2-octane diol based on total weight of the wash composition.

Fragrances, fixatives, chelators (like EDTA), opacifiers (like titanium dioxide and vegetable-derived liquid dispersions like MACKADET® OPR 2 made available from Solvay), inorganic salts (e.g., NaCl, CaCl) and exfoliants may optionally be included in the wash composition. Each of these substances may range from about 0.03 to about 5%, preferably between 0.1 and 3%, and most preferably, from 0.1 to 2% by weight of weight of the wash composition. To the extent the exfoliants are used, those selected should be of small enough particle size so that they do not impede the performance of any packaging used to dispense the compositions of this invention.

Conventional emulsifiers having an HLB of greater than 8 may optionally be used. Illustrative examples include Tween, 40, 60, 80, polysorbate 20 and mixtures thereof. Such emulsifiers, when used for water continuous systems, make up from 0.03 to 1.5% by weight of the wash composition.

When making wash composition of the present invention, the desired ingredients may be mixed with conventional apparatus under moderate shear and atmospheric conditions, with temperature being from 30 to 85° C. whereby shear continues until a homogeneous product is recovered.

The packaging for the wash composition typically is not limited as long as composition can be dispensed. In an embodiment on the invention, the wash composition is sold in a pouch, bottle, jar, tube or canister. The packaging preferably allows for infinite numbers of refilling to invariably reduce plastic waste in the environment, and most preferably, has at least 50% by weight post-consumer resin.

The Examples are provided to facilitate an understanding of the invention. They are not intended to limit the scope of the claims.

EXAMPLES

All Samples in the Examples were prepared by mixing the ingredients with moderate shear. Temperature was varied from about 40 to 70° C. and pressure while mixing was atmospheric. Carrageenan was added to the base composition (Example 1) below at the amounts identified in the Samples of Example 2 where water was modified to balance. Visual assessments of the sample wash compositions were made by trained panelists after the sample wash compositions were stored at 50° C. for two (2) weeks (Example 2). Pass is defined as no composition syneresis, and no composition malodor and/or discoloration observed by the trained panelists.

Example 1

| Ingredient | Weight % |
|---|---|
| Water | Balance |
| Tetrasodium EDTA | 0.05 |
| Carrageenan (Iota)* | See Example 2 |
| Carrageenan (Lambda)** | See Example 2 |
| Glycerin | 1.0 |
| Sodium Lauroyl Isethionate | 1.8 |
| Preservative | 0.3 |
| Sodium Lauroyl Taurate | 1.8 |
| Lauric Acid | 1.3 |
| Stearic Acid | 0.1 |
| Betaine UQS | 6.5 |
| Preservative | 0.5 |
| pH modifier | 0.2 |
| Sodium Chloride | 2.00 |
| Colorant | 0.0003 |
| Opacifier | 0.3 |
| Fragrance | 1.0 |
| Total | 100 |

*Genuvisco ® CG 131, iota carrageenan, CP KELCO
**Genuvisco ® CG 129, lambda carrageenan, CP KELCO Example 2

Final wash compositions were made by adding a hydrocolloid mixture of sulfated polysaccharide as described in the Table.

| | Lambda/Iota (weight % Active) | | | | | |
|---|---|---|---|---|---|---|
| | 0%/ 0.87% | 0.17%/ 0.7% | 0.22%/ 0.65% | 0.32%/ 0.55% | 0.42%/ 0.45% | 0.87/ 0% |
| 50° C., for 2 weeks | Fail | Stable | Stable | Stable | Stable | Fail |

As can be observed from the data provided, compositions made with a hydrocolloid mixture of sulfated polysaccharide according to the invention surprisingly passed (i.e., were stable, free of syneresis, discoloration and malodor) when stored at elevated temperatures.

We claim:
1. A wash composition comprising:
   a) 0.4 to 1.3% by weight of a hydrocolloid mixture of sulfated polysaccharide;

b) 6 to 20% by weight surfactant, the surfactant comprising an acyl isethionate, acyl taurate and betaine;
   c) 0.0 to 25% by weight polyol; and
   d) water,
   the wash composition having a viscosity of from 700 to 15,000 cps and the mixture of sulfated polysaccharide comprising lambda to iota carrageenan in a weight ratio from 1:1 to 1:7, the sulfated polysaccharide mixture being at least 50% by weight of a mixture of lambda and iota carrageenan based on total weight of the mixture of sulfated polysaccharide in the wash composition.

2. The wash composition according to claim 1, wherein the composition comprises lambda to iota carrageenan in a weight ratio from 1:1 to 1:6.

3. The wash composition according to claim 1, wherein the pH of the composition is from 4.8 to 7.5.

4. The wash composition according to claim 1, wherein the hydrocolloid mixture of sulfated polysaccharide consists of lambda and iota carrageenan in a weight ratio from 1:1 to 1:5.5.

5. The wash composition according to claim 1, wherein the hydrocolloid mixture of sulfated polysaccharide is free of kappa carrageenan.

6. The wash composition according to claim 1, wherein water makes up from 60 to 95% by weight of the composition.

7. The wash composition according to claim 1, wherein the composition comprises water soluble actives, oil soluble skin benefit agents or both.

8. The wash composition according to claim 1, wherein polyol makes up from 0.5 to 8% by weight of the composition.

9. The wash composition according to claim 1, wherein the hydrocolloid mixture of sulfated polysaccharide is at least 60% by weight a mixture of lambda and iota carrageenan based on total weight of sulfated polysaccharide in the wash composition.

10. The wash composition according to claim 1, wherein the hydrocolloid mixture of sulfated polysaccharide is from 80 to 95% by weight of a mixture of lambda and iota carrageenan based on total weight of sulfated polysaccharide in the wash composition.

11. The wash composition according to claim 1 wherein the composition further comprises an omega-3 fatty acid, omega-6 fatty acid, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, terpineol, thymol or a mixture thereof.

12. The wash composition according to claim 1 wherein the composition further comprises iodopropynyl butyl carbamate, phenoxyethanol, hydroxyacetophenone, ethylhexylglycerine, hexylene glycol, imidazolidinyl urea, sodium dehydroacetate, sodium benzoate, benzyl alcohol, sodium dehydroacetate, chlorophenesin, decylene glycol, 1,2-octanediol, N-capryloyl glycine, N-undecylenoyl glycine or a mixture thereof.

13. The wash composition according to claim 1 wherein the composition further comprises vitamin A, D, E, K, ethylhexylmethoxycinnamate, bis-ethylhexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or 4-hexyl resorcinol, 4-phenylethyl resorcinol, 4-cyclopentyl resorcinol, 4-cyclohexyl resorcinol, 4-isopropyl resorcinol, 4-cyclohexyl-5-methylbenzene-1,3-diol, 4-isopropyl-5-methylbenzene-1,3-diol or a mixture thereof.

14. The wash composition according to claim 1 wherein the composition further arginine, valine, histidine, vitamin B2, niacinamide, vitamin B6, vitamin C, ascorbyl tetraisopalmitate, magnesium ascorbyl phosphate, ascorbyl glycoside 4-ethyl resorcinol, sage, aloe vera, green tea, grapeseed, thyme, chamomile, yarrow, cucumber, liquorice, rosemary extract or a mixture thereof.

15. The wash composition according to claim 1 wherein the acyl isethionate comprises sodium lauroyl isethionate, sodium cocoyl isethionate or both, and the acyl taurate comprises sodium methyl lauroyl taurate, sodium methyl cocoyl taurate or both and the betaine comprises cocamidopropyl betaine.

16. The wash composition according to claim 15 wherein the wash composition further comprises sodium lauroyl glycinate, sodium cocoyl glycinate, sodium lauroyl glutamate, sodium cocoyl glutamate or a mixture thereof.

17. The wash composition according to claim 15 wherein the wash composition further comprises 12-hydroxystearic acid, vitamin C, niacinamide, rosemary extract or a mixture thereof.

18. The wash composition according to claim 15 wherein the wash composition further comprises a resorcinol, a retinoic acid precursor, or both.

19. The wash composition according to claim 15 wherein the wash composition has a pH from 5.5 to 7.3, and further comprises thymol, terpineol or sunscreen.

* * * * *